United States Patent [19]

Berg

[11] Patent Number: 5,763,695
[45] Date of Patent: Jun. 9, 1998

[54] SEPARATION OF 3-METHYL-1-BUTANOL FROM 1-PENTANOL BY EXTRACTIVE DISTILLATION

[76] Inventor: Lloyd Berg, 1314 S. 3rd Ave., Bozeman, Mont. 59715

[21] Appl. No.: 891,725

[22] Filed: Jul. 14, 1997

[51] Int. Cl.$^6$ ..................................... C07C 27/32
[52] U.S. Cl. .............................. 568/913; 203/44; 203/46; 203/57; 203/59; 203/60; 203/62; 203/68
[58] Field of Search ............................... 568/913; 203/57, 203/60, 62, 68, 59, 44, 46

[56] References Cited

U.S. PATENT DOCUMENTS 2,552,911  5/1951  Steitz.
2,635,072  4/1953  Eliot.
4,969,977  11/1990  Berg.

*Primary Examiner*—Gary Geist
*Assistant Examiner*—Jean F. Vollano

[57] ABSTRACT

3-Methyl-1-butanol cannot be separated from 1-pentanol by distillation or rectification because of the closeness of their boiling points. 3-Methyl-1-butanol is readily separated from 1-pentanol by extractive distillation. Effective agents are butyl benzoate, 2-undecanone and diethylene glycol methyl ether.

1 Claim, No Drawings

SEPARATION OF 3-METHYL-1-BUTANOL FROM 1-PENTANOL BY EXTRACTIVE DISTILLATION

FIELD OF THE INVENTION

This invention relates to a method for separating 3-methyl-1-butano from 1-pentanol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

3-Methyl 1-butanol and 1-pentanol boil 8 degrees apart and have a relative volatility of 1.05 which makes it impossible to separate them by conventional distillation or rectification. Table 2 shows that with an agent giving a relative volatility of 1.4 only 35 actual plates are required to get 99% purity.

TABLE 2

Theoretical and Actual Plates Required vs. Relative volatilty for 3-Methyl-1-Butanol from 1-pentanol.

| Relative Volatility | Theoretical Plates Required At Total Reflux, 99% Purity | Actual Plates Required, 75% Eff. |
|---|---|---|
| 1.3 | 34 | 46 |
| 1.4 | 26 | 35 |

OBJECTIVE OF THE INVENTION

The object of this invention is to provide a process or method of extractive distillation that will enhance the relative volatility of 3-methyl-1-butanol and 1-pentanol in their separation in a rectification column. It is a further object of this invention to identify effective extractive distillation agents that are stable and can be recycled.

SUMMARY OF THE INVENTION

The objects of this invention are provided by a process for the separation of 3-methyl-1-butanol and 1-pentanol which entails the use of certain organic compounds when employed as the agent in extractive distillation.

TABLE 3

Effective Extractive Distillation Agents For Separating 3-Methyl-1-Butanol Fom 1-Pentanol

| Compounds | Relative Volatility |
|---|---|
| None | 1.05 |
| Benzyl acetate | 1.35 |
| Methyl benzoate | 1.35 |
| Butyl benzoate | 1.4 |
| Butyl butyrate | 1.4 |
| Ethyl lactate | 1.45 |
| Hexyl formate | 1.4 |
| Isobutyl butyrate | 1.35 |
| Dibutyl phthalate | 1.35 |
| 2-Undecanone | 1.6 |
| Dodecane | 1.4 |
| Myrcene | 1.6 |
| Cymene | 1.35 |
| 1,2-Diaminocyclohexane | 1.35 |
| Nitrobenzene | 1.35 |
| 4-Ethyl morpholine | 1.37 |
| 2,6-Dimethyl morpholine | 1.45 |
| N,N-Diethylaniline | 1.35 |
| m-Cresol | 1.35 |
| p-Cresol | 1.35 |
| 2,6-Dimethylphenol | 1.35 |
| Diethylene glycol methyl ether | 1.45 |
| Morpholine | 1.4 |

DETAILED DESCRIPTION OF THE INVENTION

I have discovered that certain organic compounds will effectively increase the relative volatility between 3-methyl-1-butanol and 1-pentanol during rectification when employed as the agent in extractive distillation. They are benzyl acetate, methyl benzoate, butyl benzoate, butyl butyrate, ethyl lactate, hexyl formate, isobutyl butyrate, dibutyl phthalate, 2-undecanone, dodecane, myrcene, cymene, 1,2-diaminocyclohexane, nitrobenzene, 4-ethyl morpholine, 2,6-dimethyl morpholine, N,N-diethylaniline, m-cresol, p-cresol, 2,6-dimethylphenol, diethylene glycol methyl ether and morpholine.

THE USEFULNESS OF THE INVENTION

The usefulness of this invention can be demonstrated by referring to the data presented in Tables 1, 2 and 3. All of the successful agents show that 3-methyl-1-butanol can be separated from 1-pentanol by means of extractive distillation in a rectification column and that the ease of separation as measured by relative volatility is considerable.

WORKING EXAMPLE

1. Fifty-grams of 3-methyl-1-butanol-1-pentanol mixture and fifty grams of butyl benzoate were charged to a vapor-liquid equilibrium still and refluxed for four hours. The vapor composition was 68% 3-methyl-1-butanol and 32% 1-pentanol; the liquid composition was 60.4% 3-methyl-1-butanol and 39.6% 1-pentanol. This is a relative volatility of 1.4.

I claim:

1. A method for recovering 3-methyl-1-butanol from a mixture of 3-methyl-1-butanol and 1-pentanol which comprises distilling a mixture of 3-methyl-1-butanol and 1-pentanol in the presence of an extractive distillation agent, recovering the 3-methyl-1-butanol as overhead product and obtaining the 1-pentanol and the extractive distillation agent as bottoms product, wherein said extractive distillation agent consists essentially of one material selected from the group consisting of benzyl acetate, butyl benzoate, butyl butyrate, ethyl lactate, hexyl formate, isobutyl butyrate, dibutyl phthalate, 2-undecanone, dodecane, myrcene, cymene, 1,2-diaminocyclohexane, nitrobenzene, 4-ethyl morpholine, N,N-diethylaniline, 2,6-dimethyl morpholine, m-cresol, p-cresol, 2,6-dimethylphenol, diethylene glycol methyl ether and morpholine.

* * * * *